(12) United States Patent
Nirvanashetty et al.

(10) Patent No.: US 12,324,823 B2
(45) Date of Patent: Jun. 10, 2025

(54) SYNERGISTIC HERBAL COMPOSITION FOR SEXUAL DISORDERS

(71) Applicant: OLENE LIFE SCIENCES PRIVATE LIMITED, Chennai (IN)

(72) Inventors: Somashekara Nirvanashetty, Chennai (IN); Sanjib Kumar Panda, Chennai (IN); Vivek Anand Parachur, Chennai (IN)

(73) Assignee: OLENE LIFE SCIENCES PRIVATE LIMITED, Chennai (IN)

( * ) Notice: Subject to any disclaimer, the term of this patent is extended or adjusted under 35 U.S.C. 154(b) by 768 days.

(21) Appl. No.: 17/399,139

(22) Filed: Aug. 11, 2021

(65) Prior Publication Data

US 2021/0379134 A1  Dec. 9, 2021

Related U.S. Application Data

(63) Continuation-in-part of application No. PCT/IN2020/050136, filed on Feb. 11, 2020.

(30) Foreign Application Priority Data

Feb. 11, 2019 (IN) .............................. 201941005346

(51) Int. Cl.
| | | |
|---|---|---|
| *A61K 36/48* | (2006.01) | |
| *A61K 9/48* | (2006.01) | |
| *A61K 31/198* | (2006.01) | |
| *A61K 36/28* | (2006.01) | |
| *A61K 36/38* | (2006.01) | |
| *A61K 36/41* | (2006.01) | |
| *A61K 36/63* | (2006.01) | |
| *A61K 36/81* | (2006.01) | |
| *A61K 36/8965* | (2006.01) | |
| *A61P 15/10* | (2006.01) | |

(52) U.S. Cl.
CPC ............ *A61K 36/48* (2013.01); *A61K 9/4833* (2013.01); *A61K 9/485* (2013.01); *A61K 9/4866* (2013.01); *A61K 31/198* (2013.01); *A61K 36/28* (2013.01); *A61K 36/38* (2013.01); *A61K 36/41* (2013.01); *A61K 36/63* (2013.01); *A61K 36/81* (2013.01); *A61K 36/8965* (2013.01); *A61P 15/10* (2018.01)

(58) Field of Classification Search
None
See application file for complete search history.

(56) References Cited

U.S. PATENT DOCUMENTS

| | | | |
|---|---|---|---|
| 9,486,482 | B2 | 11/2016 | Chaudhary et al. |
| 2002/0037862 | A1* | 3/2002 | Rohdewald ............ A61P 21/02 514/565 |
| 2008/0138448 | A1* | 6/2008 | Heuer .................. A61K 31/522 424/746 |

FOREIGN PATENT DOCUMENTS

| | | | |
|---|---|---|---|
| IN | 48/2006 | | 12/2006 |
| IN | 23/2007 | | 6/2007 |
| IN | 430/DEL/2009 | | 9/2010 |
| IN | 549/DEL/2011 | A | 4/2011 |
| IN | 33/2012 | | 8/2012 |
| IN | 27/2016 | * | 8/2014 |
| IN | 17/2015 | | 4/2015 |
| IN | 201621011362 | | 11/2017 |

OTHER PUBLICATIONS

Stanley E. Althof, PhD, et al., "An Update of the International Society of Sexual Medicine's Guidelines for the Diagnosis and Treatment of Premature Ejaculation;" Sexual Medicine published by Wiley Periodicals, Inc. on behalf of International Society for Sexual Medicine; 31 pages; 2014.
Ege Can Serefoglu, MD, et al., "An Evidence-Based Unified Definition of Lifelong and Acquired Premature Ejaculation: Report of the Second International Society for Sexual Medicine Ad Hoc Committee for the Definition of Premature Ejaculation;" Sexual Medicine published by Wiley Periodicals, Inc. Sex Med on behalf of International Society for Sexual Medicine; 19 pages; 2014.
Kavitha C., et al., "Amazing bean "Mucuna Pruriens": A comprehensive review;" Amazing Bean "Mucuna pruriens": A Comprehensive Review; vol. 8(2), pp. 138-143, Jan. 10, 2014; 6 pages.
Sachin Wankhede, et al., "Beneficial Effects of Fenugreek Glycoside Supplementation in Male Subjects during Resistance Training: A Randomized Controlled Pilot Study," Journal of Sports and Health Science 5; 2016; 7 pages.
Anuj Maheshwari, et al., "Efficacy of FurosapTM, a Novel Trigonella Foenum-graecum Seed Extract, in Enhancing Testosterone Level and Improving Sperm Profile in Male Volunteers," International Journal of Medical Sciences; 2017, vol. 14, 9 pages.
Bichitra N. Nayak, PhD, et al., "Herbal Therapy for Men with Erectile Eysfunction," Curr Res Cardiol vol. 2 No. 1 Spring 2015; 5 pages.
Helen E. Fisher, et al., "Romantic Love: A Mammalian Brain System for Mate Choice," Philosophical Transactions of The Royal Society; 2006; 14 pages.
Sachin Wankhede, et al., Examining the Effect of Withania Somnifera Supplementation on Muscle Strength and Recovery: A Randomized Controlled Trial; Journal of the International Society of Sports Nutrition (2015); 11 pages.
HG/2314; Key Attributes of TKDL; Title of Traditional Knowledge Resource; Aug. 16, 2021; 7 pages.

(Continued)

*Primary Examiner* — Susan Hoffman
(74) *Attorney, Agent, or Firm* — Kramer & Amado, P.C.

(57) ABSTRACT

The invention disclosed herein is a synergistic herbal composition comprising extracts of *Mucuna pruriens, Cynara cardunculus, Trigonella foenum graecum, Withania somnifera* and L-arginine along with pharmaceutically acceptable excipients, having libido enhancing, testosterone levels increasing and ejaculation delaying properties. The present invention also disclosed herein a process for preparation of said composition.

20 Claims, 2 Drawing Sheets

(56) References Cited

OTHER PUBLICATIONS

Kamla Kant Shukla, et al., "Mucuna Pruriens Improves Male Fertility by its Action on the Hypothalamus-pituitary-gonadal Axis," Nov. 2008; 8 pages.

Roy Baumeister, et al., Is There a Gender Difference in Strength of Sex Drive? Theoretical Views, Conceptual Distinctions, and a Review of Relevant Evidence, Aug. 2001, 33 pages.

International Search Report and Written Opinion for corresponding PCT/IN2020/050136 mailed on Jun. 10, 2020.

Nagendra Singh Chauhan et al., "A Review of Plants Used for Improvement of Sexual Performance and Viri~lity," Hindawi Publishing Corporation, BioMed Research International, vol. 2014, 19 pgs., http://dx.doi.org/10.1155/2014/868062.

Adrian L. Lopresti et al., "A Randomized, Double-Blind, Placebo-Controlled, Crossover Study Examining the Hormonal and Vitality Effects of Ashwangandha (*Withania somnifera*) in Aging, Overweight Males," American Journal of Men's Health, Mar.-Apr. 2019, pp. 1-15, 2019.

\* cited by examiner

SYNERGISTIC HERBAL COMPOSITION FOR SEXUAL DISORDERS

CROSS-REFERENCE TO RELATED APPLICATIONS

This is a Continuation-In-Part of International Application No. WO/IN2020/050136, filed Feb. 11, 2020, which in turn claims priority to Indian Application No. 201941005346, filed Feb. 11, 2019. The entire disclosure of each prior application is incorporated by reference herein in its entirety.

TECHNICAL FIELD OF THE INVENTION

The present invention relates to a synergistic composition comprising herbal extracts having libido enhancing, testosterone level increasing and ejaculation delaying properties. The present invention also relates to a process for preparation of said composition.

BACKGROUND AND PRIOR ART OF THE INVENTION

Sexual desires are often an important factor in the formation and maintenance of intimate relationships in humans. Loss of sexual desire is increasingly recognized as a consequence of many disease processes, and one that can have a significant negative impact on quality of life. Sexual desire disorders are leading to a great deal of morbidity in relationships. A lack or loss of sexual desire can adversely affect relationships.

Libido is a person's overall sexual drive or desire for sexual activity. Libido is influenced by biological, psychological and social factors. Biologically, the sex hormones and associated neurotransmitters that act upon the nucleus accumbens (primarily testosterone and dopamine, respectively) regulate libido in humans (Fisher H E et al.; *Philos. Trans. R. Soc. Lond. B. Biol. Sci.* 2006 Dec. 29; 361 (1476): 2173-86). Social factors, such as work and family, and internal psychological factors, such as personality and stress, can affect libido. Libido can also be affected by medical conditions, medications, lifestyle and relationship issues. A 2001 review found that on average, men have a higher desire for sex than women (Roy F. Baumeister et. al., *Personality and Social Psychology Review* 2001, Vol 5, No. 3, 242-273).

Erectile dysfunction (ED) is also one of the most common conditions affecting men's sexual desire. ED is defined as the persistent inability to achieve or maintain an erection adequate for satisfactory sexual activity. The most important organic causes of impotence are cardiovascular disease and diabetes, neurological problems, hormonal insufficiencies and drug side effects.

Libido and erectile dysfunction are interconnected. Stress, in particular, can interfere with body's hormone levels and result in a low libido. The arteries can also narrow and restrict blood flow in response to stress, which can also lead to erectile dysfunction.

Premature ejaculation (PE) is one of the most prevalent male sexual disorders. It is defined by the International Society for Sexual Medicine (ISSM) as a male sexual dysfunction that is characterized by: "Ejaculation that always or nearly always occurs prior to or within about 1 minute of vaginal penetration from the first sexual experience [Lifelong Premature Ejaculation (LPE)] or a clinically significant reduction in latency time, often to about 3 minutes or less [Acquired Premature Ejaculation (APE)]; the inability to delay ejaculation on all or nearly all vaginal penetrations". The premature ejaculation is a complex phenomenon that is influenced by biological, physiological and psychological status of the individual. The Abnormality in hormone levels, any change in medications related to the neurotransmitter blockers/activators, prolong inflammation and infection of the prostate or urethra are the main biological causes. Beside them the genetic inheritance also plays the main role. Diabetes, multiple sclerosis, prostate disease, high blood pressure (hypertension), thyroid problems, illicit drug use and excessive alcohol consumption are the most important medical causes for PE. Premature/early sexual experiences, sexual abuse, the poor body image, depression or anxiety and fearing of premature ejaculation and such factors related to sexual dysfunction could be the psychological reasons for premature ejaculation in the males. There is no accurate treatment for PE in present scenario, but, some of the potentially effective therapies for the management of PE are existing. The topical anaesthetic creams, selective serotonin reuptake inhibitors (SSRIs) and phosphodiesterase type-5 (PDE-5) inhibitors have been fairly well studied for application in PE.

Presently, in market there are numerous aphrodisiac formulations, both herbal and synthetic. The interest on herbal remedies and their utilization have been increasing rapidly in recent years due to their higher safety profile and natural origin. These herbal remedies provide better medications to physiological, neurological or fertility disorders.

There are various existing marketed herbal formulations which concerns to provide solution for sexual desire, erectile dysfunction and premature ejaculation in men. However, an effective solution in the form of a unique formulation is not provided in the art which offers the desired results. Most of the clinical studies showed insignificant results over placebo. Also, the existing formulations may cause side effects such as heart racing, insomnia, anxiety and irritability in men.

Further, there are several patented literature available on herbal compositions that can treat sexual disorders.

Patent Application No. 4002/CHE/2014 discloses a synergistic fertility herbal formulation for men comprises an effective group of compounds derived from natural sources preferably plants, fruits, seeds, tubers and flower buds of *Hordeum vulgare, Mucuna pruriens, Daucus carota, Foeniculum vulgare, Withania somnifera, Crocus sativus, Safed musli, Trigonella foenum graecum linn, Piper nigrum* and *Ocimum sanctum*. The synergistic fertility herbal formulation comprises various naturals extracts are used for treating low sperm count and low sperm motility and also act as male libido enhancer and energy supplement for men without any side effects.

The invention disclosed in 4002/CHE/2014 addresses a problem of low sperm count/low sperm motility resulting into male infertility and offers a solution by providing herbal fertility formulation that increases sperm count and sperm motility. The said formulation comprises around 10 different plant extracts with less than 50 mg concentration of actives.

Patent Application No. 549/DEL/2011 discloses aphrodisiac herbal composition comprises extracts or particulate material from the plants *Withania somnifera, Asparagus racemosus, Mucuna pruriens, Glycyrrhiza glabra, Trigonella foenum, Zingiber officinale, Tribulus terrestris, Asphalt* and *Curculigo orchodes*. The said aphrodisiac herbal composition is specifically for females suffering from lack of sexual desire and an arousal disorders.

Patent Application No. 2642/MUM/2009 provides a composition for supporting sexual function and general wellbeing comprising combination of herbal extracts including extracts of *Tribulus terrestris, Mucuna pruriens, Ginkgo biloba* and Yohimbe bark with L-Arginine and Zinc to provide the synergistic activity on physiological parameters of libido, erection, orgasm and improvement in semen parameters.

Patent No. 241602 (1651/CHE/2006) discloses an ayurvedic medical preparation named "MUSLIPOWER X-TRA" where in the chemical constituents such as alakalloids, minerals and protein extracts of 1. *Chlorophylum borivillianum* (safed mush) 2. *Mucuna purita* (kapikachu) 3. *Muringa oleifra* (siguru) 4. *Withania somnifera* (Aswagandha) 5. *Embilica officinalis* (amalaki) 6. *Tribulus terrestris* (njerinjil) 7. *Hygrophila auriculata* (vayalchully) 8. *Myristica* Qathika) are extracted in a unique manner and are mixed at a particular quantity to obtain this unique ayurvedic medicine that is used for male and female sexual inadequacies.

Patent Application No. 370/DEL/2005 discloses a composition for the treatment of premature ejaculation. The composition comprises a synergistic mixture of following herbal extracts and chemicals, each one of said ingredients being present in an amount of from 0.01 to 75% by wt: Cowhage Root (Atmagupta—*Mucuna prurita*), Winter Cherry (Ashwagandha—*Withania somnifera*), Pellitory Root (Akarakarabha—*Anacyclus pyrethrum*), Staff Tree Seed (Jyotishmati—*Celastrus paniculatus*), Water Chestnut (Kaseru—*Scirpus kysoor*), Milky Yam Root (Vidari—*Pueraria tuberosa*), Cinnamon Bark (Tvak—*Cinnamoinum zeylanicum*), Camphor (Karpur—*Cinnamomum camphora*), Carbomer—Carbopol 940, Sodium Propyl Paraben, and Lignocaine Hydrochloride.

Patent Application No. 1380/MUM/2009 (U.S. Pat. No. 9,486,482) discloses a synergistic herbal composition comprising extracts of herbal ingredients of *Tribulus terrestris, Withania somnifera, Curculigo orchioides, Mucuna pruriens, Asparagus adscendens, Asteracantha longifolia,* Asphaltum, and optionally the extracts of *Piper longum* and *Anacyclus pyrethrum* for the treatment of disorders associated with Male Sexual Dysfunction.

Patent Application No. IN201621011362 relates to nutraceutical supplement comprising the effective amount of *Chlorophytum* arundinacium, *Withania somnifera, Mucuna pruriens, Pueraria tuberosa, Bombax ceiba, Phoenix dactylifera, Cicer arientinum, Hordeum vulgare* and *Saccharum officinarum* for use in prophylaxis or treatment of aphrodisiac activity.

Patent Application No. 3119/DEL/2013 discloses an herbal aphrodisiac composition for men which also act as tonic to treat other sexual dysfunction which comprises of *Trigonella foenum-graecum* 100 mg to 1000 mg, *Tribulus terrestris* 50 mg to 500 mg, *Chlorophytum borivillianum* 50 mg to 500 mg, Asphaltum punjabianum 50 mg to 250 mg.

Patent No. 298193 (430/DEL/2009) relates to an improved method for manufacturing of *Mucuna pruriens*, seeds extract having L-Dopa content least 40% by HPLC analysis, and also relates to the use of *Mucuna pruriens* seeds, for preparation of a potential pharmaceutical formulation for treating Parkinson disease, male erectile dysfunction problem and as food supplements.

In case of herbal medicaments that treat sexual disorders a single herb used in the composition can provide a particular effect and cannot address the overall sexual difficulties. The available herbal medicines are either contain single herb as an active in large amount or a combination of different herbs, which fails to provide a complete action on physiological parameters such as libido, testosterone levels, erection and delay in ejaculation.

Premature ejaculation (PE) is multifactorial disease with several causes. PE is a complex phenomenon that is influenced by biological, physiological and psychological status of the individual. Hence, no single herb product and inappropriately designed mix of herbs will give benefits in treating PE. A right mix of herbs which targets all of the PE causes may be suitable for the treatment of PE. Therefore, there is a need in the art to provide an herbal composition which overcome the problem associated with the prior art. Also, there is a need for a composition that delivers comprehensive and complete solution for libido, increasing testosterone level, decreasing anxiety and treating premature ejaculation without any side effects.

The plant *Mucuna pruriens* belongs to the family Leguminosae. Seeds of this plant contain high concentration of L-DOPA, a precursor for neurotransmitter Dopamine. Dopamine is an important brain chemical involved in mood, sexuality and movement. *Mucuna pruriens* reactivates the N-oxidant defence mechanism, helps in the management of stress, improves mood and improves semen quality. *Mucuna pruriens* increases serotonin levels in the body which is required for delaying the ejaculation.

The *Cynara cardunculus* var. *scolymus* (artichoke) is a variety of a species of thistle cultivated as a food and the plant parts used is the leaf. Artichoke contains the bioactive agents such as cynarine and luteolin. Luteolin is a high affinity phosphodiesterase (PDE) inhibitor. Flavonoids from artichoke extract have been report as a Nitric oxide enhancer by up-regulating the endothelial nitric-oxide synthase (eNOS). Enhance NO level will relax the smooth muscle and increase the blood flow leading to penile erection. *Cynara cardunculus* is not reported in the art for increasing testosterone levels.

The plant *Trigonella foenum graecum* i.e. Fenugreek contains phytochemicals called saponins and sapogenins, which are responsible for increasing sex hormone, testosterone and hence libido.

*Withania somnifera* is known commonly as ashwagandha. Ashwagandha is typically used as an "adaptogen" (for stress and anxiety relief). The roots of the plant contain steroid alkaloids and steroidal lactone, which are the main constituents of ashwagandha; these compounds are referred to as withanolides.

L-arginine complements *Cynara* by increasing the levels of nitric oxide in the body which is required for proper penile erection.

Considering the above-mentioned properties of said plants, the inventors of present invention have prepared a synergistic composition from extracts of said plant, which boost testosterone levels, enhanced libido, lowers anxiety, improves erection and delay the ejaculation.

SUMMARY OF THE INVENTION

Accordingly, it is an object of the present invention is to develop a composition comprises synergistic combination of safe herbal ingredients for aiding men's sexual wellness.

Another object of the present invention is to provide a synergistic composition that enhances sustained libido and erection through boosting testosterone levels without any side effects.

Yet another object of the present invention is to provide a synergistic composition that increases Libido, reduces anxiety, improves penile Erection and increases Intra-vaginal ejaculation latency time (IELT) (delaying ejaculation) leading superior sexual experience and sexual stamina.

In various embodiments, the present disclosure relates to an herbal composition comprising an extract of *Mucuna pruriens*, an extract of *Cynara cardunculus*, an extract of *Trigonella foenum graecum*, an extract of *Withania somnifera*, L-arginine, and a pharmaceutically acceptable excipient, wherein the herbal composition meets at least one of the following conditions:
the extract of *Mucuna pruriens* and at least one of the extract of *Cynara cardunculus*, the extract of *Trigonella foenum graecum*, and the extract of *Withania somnifera* are present in the herbal composition in a first ratio of 1:2 by weight; and
the extract of *Cynara cardunculus* and at least one of the extract of *Trigonella foenum* graecum, and the extract of *Withania somnifera* are present in the herbal composition in a second ratio of 1:1 by weight.

The present disclosure relates to an herbal composition comprising an extract of *Mucuna pruriens*, an extract of *Cynara cardunculus*, an extract of *Trigonella foenum graecum*, an extract of *Withania somnifera*, L-arginine, and a pharmaceutically acceptable excipient, wherein:
the extract of *Mucuna pruriens* and the extract of *Cynara cardunculus* are present in the herbal composition in the first ratio of 1:2 by weight;
the extract of *Mucuna pruriens* and the extract of *Cynara cardunculus* are present in the herbal composition in the first ratio of 1:2 by weight; and the extract of *Mucuna pruriens* and at least one of the extract of *Trigonella foenum graecum* and the extract of *Withania somnifera* are also present in the herbal composition in the first ratio of 1:2 by weight;
the extract of *Mucuna pruriens* and the extract of *Trigonella foenum graecum* are present in the herbal composition in the first ratio of 1:2 by weight;
the extract of *Mucuna pruriens* and the extract of *Withania somnifera* are present in the herbal composition in the first ratio of 1:2 by weight;
the extract of *Cynara cardunculus* and the extract of *Trigonella foenum graecum* are present in the herbal composition in the second ratio of 1:1 by weight;
the extract of *Cynara cardunculus* and the extract of *Withania somnifera* are present in the herbal composition in the second ratio of 1:1 by weight; and/or
the extract of *Trigonella foenum graecum* and the extract of *Withania somnifera* are present in the herbal composition in the second ratio of 1:1 by weight.

In various embodiments, the present disclosure relates to an herbal composition comprising an extract of *Mucuna pruriens*, an extract of *Cynara cardunculus*, an extract of *Trigonella foenum graecum*, an extract of *Withania somnifera*, L-arginine, and a pharmaceutically acceptable excipient, wherein the herbal composition meets at least one of the following conditions:
L-arginine and the extract of *Mucuna pruriens* are present in a third ratio of 1:1 by weight; and
L-arginine and at least one of the extract of *Cynara cardunculus*, the extract of *Trigonella foenum graecum*, and the extract of *Withania somnifera* are present in the herbal composition in a fourth ratio of 1:2 by weight.

The present disclosure relates to an herbal composition comprising an extract of *Mucuna pruriens*, an extract of *Cynara cardunculus*, an extract of *Trigonella foenum graecum*, an extract of *Withania somnifera*, L-arginine, and a pharmaceutically acceptable excipient, wherein the pharmaceutically acceptable excipient is present in the dosage form in an amount of 40 mg to 100 mg.

Various embodiments disclosed herein relate to an herbal composition, wherein the composition is a dosage form, and the dosage form includes:
a) an extract of *Mucuna pruriens* in an amount of 40 to 80 mg, or 50 to 72 mg;
b) an extract of *Cynara cardunculus* in an amount of 90 to 150 mg, or 100 to 144 mg;
c) an extract of *Trigonella foenum graecum* in an amount of 90 to 150 mg, or 100 to 144 mg;
d) an extract of *Withania somnifera* in an amount of 90 to 150 mg, or 100 to 144 mg;
e) L-arginine in an amount of 40 to 80 mg, or 50 to 72 mg; and
f) a pharmaceutically acceptable excipient.

The dosage form may be selected from tablets, capsules, granules, and pills.

The present disclosure relates to an herbal composition comprising an extract of *Mucuna pruriens*, an extract of *Cynara cardunculus*, an extract of *Trigonella foenum graecum*, an extract of *Withania somnifera*, L-arginine, and a pharmaceutically acceptable excipient selected from the group consisting of binders, glidants, lubricants, diluents, disintegrants, emulsifying agents, anti-caking agents, anti-adherents, granulating agents, and mixtures thereof. In various embodiments, the pharmaceutically acceptable excipient comprises a mixture of 40 to 70 mg microcrystalline cellulose and 4 to 8 mg silicon dioxide. In various embodiments, the pharmaceutically acceptable excipient is present in the dosage form in an amount of 40 mg to 100 mg.

Various embodiments disclosed herein relate to a process for preparation of an herbal composition, by;
a) sieving and weighing an extract of *Mucuna pruriens*, an extract of *Cynara cardunculus*, an extract of *Trigonella foenum graecum*, an extract of *Withania somnifera*, and L-Arginine;
b) after the step of sieving and weighing, blending the extract of *Mucuna pruriens*, the extract of *Cynara cardunculus*, the extract of *Trigonella foenum graecum*, the extract of *Withania somnifera*, and L-Arginine for 5 minutes at 25 rpm to produce a blended mixture;
c) adding a pharmaceutically acceptable excipient to the blended mixture, followed by blending for 10 minutes at 25 rpm to obtain a homogenized mixture; and
d) filling the homogenized mixture into a capsule shell/sachets to obtain the dosage form.

Various embodiments disclosed herein relate to a method of treating a sexual disorder by at least one of increasing testosterone levels, enhancing erection, reducing anxiety, and delaying ejaculation, by administering an herbal composition including an extract of *Mucuna pruriens*, an extract of *Cynara cardunculus*, an extract of *Trigonella foenum graecum*, an extract of *Withania somnifera*, L-arginine to a subject in need thereof.

Various embodiments disclosed herein relate to an herbal composition comprising:
a first extract which may be an extract of *Mucuna pruriens*, an extract of *Rhodiola Rosea*, an extract of horny goat weed, an extract of *Asparagus racemosus*, an extract of *Hypericum perforatum*, an extract of *Butea superba*, an extract of *Griffonia simplicifolia*, an extract of *muira puma*, an extract of Damiana, or a mixture thereof;

an extract of *Cynara* cardunculus,
an extract of *Trigonella foenum graecum*,
an extract of *Withania somnifera*,
L-arginine, and
a pharmaceutically acceptable excipient.

In various embodiments, the extract of *Cynara cardunculus* and at least one of the extract of *Trigonella foenum graecum* and the extract of *Withania somnifera* are present in the herbal composition in a second ratio of 1:1 by weight;
the extract of *Trigonella foenum graecum* and the extract of *Withania somnifera* are present in the herbal composition in the second ratio of 1:1 by weight; and/or
the first extract and at least one of the extract of *Cynara cardunculus*, the extract of *Trigonella foenum graecum*, and the extract of *Withania somnifera* are present in the herbal composition in a first ratio of 1:2 by weight.

Accordingly, in an aspect, the present invention discloses a synergistic composition comprising herbal extracts of *Mucuna pruriens, Cynara cardunculus, Trigonella foenum graecum, Withania somnifera* and L-arginine along with pharmaceutically acceptable excipients, having libido enhancing, testosterone increasing, erection enhancing, anxiety reducing and ejaculation delaying properties, collectively treating premature ejaculation.

In another aspect, the synergistic composition of the present invention boosts testosterone levels thereby provide long term benefits in low sex drive and libido and in premature ejaculation without any side effects.

In yet another aspect, the present invention discloses a process for preparation of present synergistic herbal composition.

DETAILED DESCRIPTION OF THE INVENTION

The invention will now be described in detail in connection with certain preferred and optional embodiments, so that various aspects thereof may be more fully understood and appreciated.

Source and Geographical Origin of the Biological Material Used in the Invention:

*Mucuna pruriens*
Source: Sami Labs Limited, 19/1, $1^{st}$ Main Rd, $2^{nd}$ Phase, Nalagadderanahalli, Peenya, Bengaluru, Karnataka 560058, India.
Geographical Origin: Native to Africa and tropical Asia and the Caribbean. In India, it is found in the Himalayas and Western Ghats.

*Cynara* cardunculus
Source: S V Agrofood, India 503/C, Panavally, P.O., Cherthala, Alappuzha, Kerala-688 526, India.
Geographical Origin: Native to western and central Mediterranean region.

*Trigonella foenum graecum*
Source: Sami Labs Limited, 19/1, $1^{st}$ Main Rd, $2^{nd}$ Phase, Nalagadderanahalli, Peenya, Bengaluru, Karnataka 560058, India.
Geographical Origin: Native to Western Mediterranean and spread throughout the Mediterranean region.

*Withania somnifera*
Source: Sami Labs Limited, 19/1, $1^{st}$ Main Rd, $2^{nd}$ Phase, Nalagadderanahalli, Peenya, Bengaluru, Karnataka-560058, India.
Geographical Origin: Native to drier parts of India. Also found in Nepal, China and Yemen.

L-Arginine
L-arginine is of synthetic origin and is procured from K P Manish Global Ingredients Pvt. Ltd. 41, Raghunayakulu Street, Park Town, Chennai-600003, Tamil Nadu India.

The present invention provides a synergistic composition comprising herbal extracts of *Mucuna pruriens, Cynara cardunculus, Trigonella foenum graecum, Withania somnifera* and L-arginine along with pharmaceutically acceptable excipients, wherein said composition is having libido enhancing, testosterone increasing, erection enhancing, anxiety reducing and ejaculation delaying properties at the same time.

In the present invention, seeds of *Mucuna pruriens*, leaves of *Cynara cardunculus*, seeds of *Trigonella foenum graecum* and whole plant of *Withania somnifera* are used for preparing the respective extracts. The herbal extracts are prepared by using solvents selected from ethanol, methanol and water.

L-arginine used in the composition of present invention is an amino acid that helps to make proteins. L-arginine is important for the production of nitric oxide (NO) in the body which is required for proper erectile of penis. It exerts its activity through vasodilation, which increases the blood flow into the penile arteries leading to the penile erection. Healthy blood flow to the arteries of the penis is essential for normal erectile function.

Accordingly, in one embodiment, the present invention discloses a synergistic composition comprising herbal extracts of;
a) *Mucuna pruriens* in an amount of 40 to 80 mg;
b) *Cynara cardunculus* in an amount of 90 to 150 mg;
c) *Trigonella foenum graecum* in an amount of 90 to 150 mg;
d) *Withania somnifera* in an amount of 90 to 150 mg;
e) L-arginine in an amount of 40 to 80 mg of the total weight of the composition and pharmaceutically acceptable excipients.

In another embodiment, the present invention discloses a synergistic composition comprising herbal extracts of;
a) *Mucuna pruriens* in an amount of 50 mg;
b) *Cynara cardunculus* in an amount of 100 mg;
c) *Trigonella foenum graecum* in an amount of 100 mg;
d) *Withania somnifera* in an amount of 100 mg;
e) L-arginine in an amount of 50 mg of the total weight of the composition and pharmaceutically acceptable excipients.

In another embodiment, the present invention discloses a synergistic composition comprising herbal extracts of;
a) *Mucuna pruriens* in an amount of 72.22 mg;
b) *Cynara cardunculus* in an amount of 144.44 mg;
c) *Trigonella foenum graecum* in an amount of 144.44 mg;
d) *Withania somnifera* in an amount of 144.44 mg;
e) L-arginine in an amount of 72.22 mg of the total weight of the composition and pharmaceutically acceptable excipients.

Various embodiments disclosed herein relate to an herbal composition comprising:
a first extract selected from the group consisting of an extract of *Mucuna pruriens*, an extract of *Rhodiola rosea*, an extract of horny goat weed, an extract of *Asparagus racemosus*, an extract of *Hypericum perforatum*, an extract of *Butea superba*, an extract of

*Griffonia simplicifolia*, an extract of *muira puma*, an extract of Damiana, and a mixture thereof;
an extract of *Cynara cardunculus*,
an extract of *Trigonella foenum graecum*,
an extract of *Withania somnifera*,
L-arginine, and
a pharmaceutically acceptable excipient.

In various embodiments, the extract of *Cynara cardunculus* and at least one of the extract of *Trigonella foenum graecum* and the extract of *Withania somnifera* are present in the herbal composition in a second ratio of 1:1 by weight;
the extract of *Trigonella foenum graecum* and the extract of *Withania somnifera* are present in the herbal composition in the second ratio of 1:1 by weight; and/or
the first extract and at least one of the extract of *Cynara cardunculus*, the extract of *Trigonella foenum graecum*, and the extract of *Withania somnifera* are present in the herbal composition in a first ratio of 1:2 by weight.

Accordingly, in one embodiment, the present invention discloses a synergistic composition comprising herbal extracts of:
a) a first extract which may be an extract of *Mucuna pruriens*, an extract of *Rhodiola rosea*, an extract of horny goat weed, an extract of *Asparagus racemosus*, an extract of *Hypericum perforatum*, an extract of *Butea superba*, an extract of *Griffonia simplicifolia*, an extract of *muira puma*, an extract of Damiana, or a mixture thereof, the first extract being present in an amount of 40 to 80 mg;
b) *Cynara cardunculus* in an amount of 90 to 150 mg;
c) *Trigonella foenum graecum* in an amount of 90 to 150 mg;
d) *Withania somnifera* in an amount of 90 to 150 mg;
e) L-arginine in an amount of 40 to 80 mg of the total weight of the composition and pharmaceutically acceptable excipients.

The pharmaceutically acceptable excipients are selected from binder, glidants, lubricants, diluents, disintegrants, emulsifying agents, anti-caking agents, anti-adherents and granulating agents and the like. Said excipients are present in an amount of 40-70 mg of the total weight of the composition.

The pharmaceutical acceptable excipients used in present invention are Microcrystalline Cellulose and Silicon dioxide in an amount of 40 to 70 mg and 4 to 8 mg, respectively of total weight of the composition.

In another embodiment, the present composition can be formulated into tablet, capsule, granules, pills and the like, preferably a capsule.

In yet another embodiment, the present invention discloses a process for preparation of present synergistic herbal composition comprising:
a) Sieving and weighing required quantities of *Mucuna pruriens* extract, *Cynara cardunculus* extract, *Trigonella foenum graecum* extract, *Withania somnifera* extract and L-Arginine separately;
b) blending all the raw material of step (a) for 5 minutes at 25 rpm;
c) adding microcrystalline cellulose and silicon dioxide into step (b) followed by blending for 10 minutes at 25 rpm to obtained homogenized mixture;
d) filling the homogenized mixture of step (c) into size "0" capsule using capsule filling machine to obtain final product.

In yet another embodiment, the synergistic composition of present invention enhances sustained libido and erection through boosting testosterone levels.

In yet another embodiment, the synergistic composition of present invention increases intra-vaginal ejaculation latency time (IELT) leading superior sexual experience and sexual stamina; and also providing long term benefits in people/animal with low sex drive, low libido and in premature ejaculation without any side effects.

Figure 1:
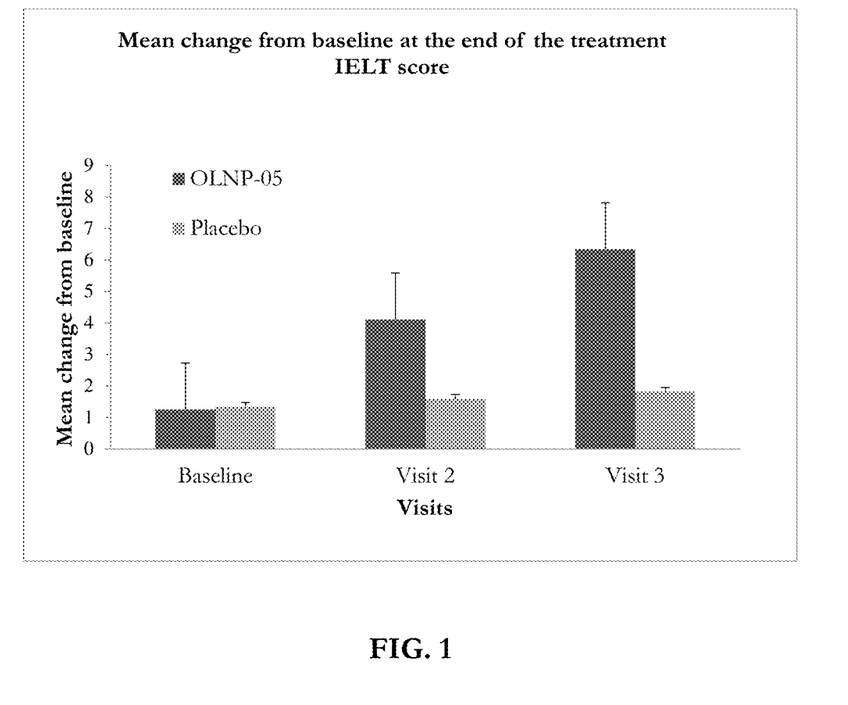
FIG. 1: Mean change from baseline in IELT subscale score at the end of the treatment
Figure 2:
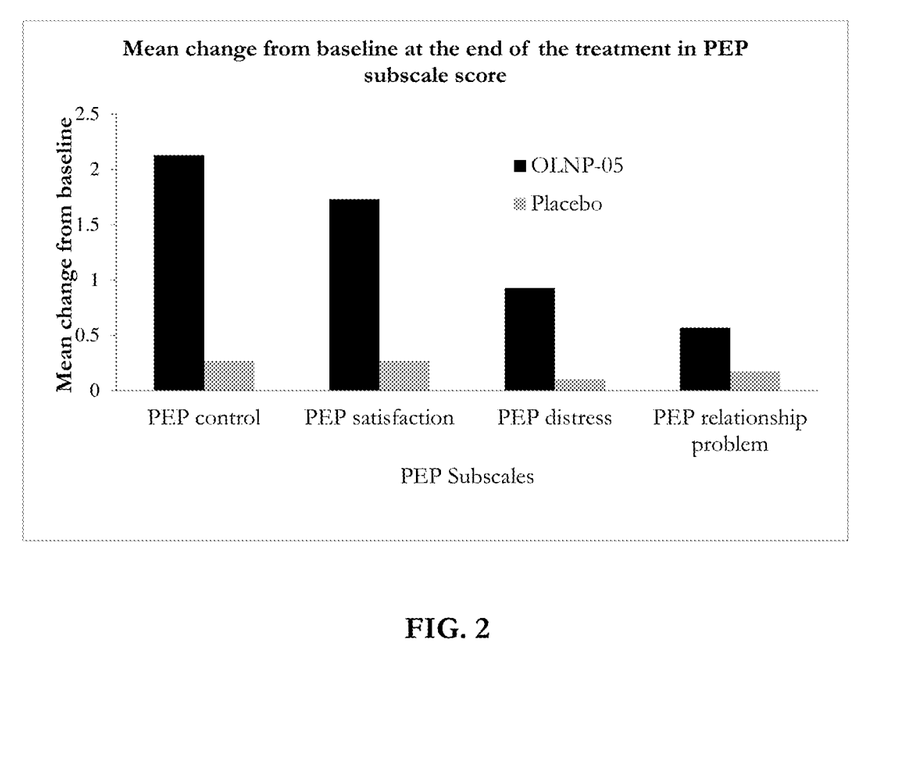
FIG. 2: Mean change from baseline in PEP subscale score at the end of the treatment

In another embodiment, the present invention demonstrates the efficacy of present composition (Example 2, coded as OLNP-05) versus placebo for the treatment of subjects with premature ejaculation (PE). There was a significant increase in IELT (Intra-vaginal Ejaculatory Latency Time) score in the OLNP-05 group as compared to placebo ($p<0.05$) (FIG. 1 and Table 2). The PEP (Premature Ejaculation Profile) score was found to be significantly improved in the OLNP-05 group, as compared to placebo treatment group. The subjects in the OLNP-05 treatment group reported significantly ($p<0.05$) greater improvement in PEP subscale score includes PEP control, PEP satisfaction, PEP distress and PEP relationship problems (FIG. 2 and Table 2).

In another embodiment, the present invention discloses an improvement in CGI-I (Clinical Global Impression-Improvement scale) in different visits. From Table 3, it is observed that, a greater proportion of mean in the OLNP-05 treated group, were found to be 'Much improved' category in the CGI-I assessment.

In another embodiment, OLNP-05 was found to be very safe and well tolerated in the clinical study.

In another embodiment, the present invention discloses acute oral toxicity study of the present composition. It is observed from Table 4 that, no clinical signs of toxicity and mortalities were observed in any of the dosed animals. Further, Table 5 depicts that, all animals in the test revealed physiologically normal increase in body weights during the observation period and Table 6 depicts that, no gross pathologically changes were observed in any of the animals.

In another embodiment, the present invention discloses Testosterone Study of the present composition. The synergy of the present composition (Example 2, OLNP-05) is achieved by a significant increase in total testosterone level and in free testosterone level over an individual extract and the same was demonstrated in Table 7.

In another embodiment, the present invention demonstrates the efficacy study of present composition (Example 2, coded as OLNP-05) versus capsule composition of U.S. Pat. No. 9,486,482 (Example 3, Table 6). The study indicates that the percentage improvement in the ejaculation profile is better in OLNP-05 compare to capsule composition of U.S. Pat. No. 9,486,482 and the same was depict in Table 8.

In yet another embodiment, the present invention discloses method of treating sexual disorders selected from enhancing libido, increasing testosterone levels, enhancing erection, reducing anxiety and delaying ejaculation comprising administering a synergistic herbal composition comprising extracts of *Mucuna pruriens, Cynara cardunculus, Trigonella foenum graecum, Withania somnifera* and L-arginine along with pharmaceutically acceptable excipients, to a subject in need thereof.

In yet another embodiment, the present invention discloses a synergistic herbal composition comprising extracts of *Mucuna pruriens, Cynara cardunculus, Trigonella foenum graecum, Withania somnifera* and L-arginine along with pharmaceutically acceptable excipients, useful for the treatment of sexual disorders selected from enhancing libido, increasing testosterone levels, enhancing erection, reducing anxiety and delaying ejaculation.

EXAMPLES

Some typical examples illustrating the embodiments of the present invention are provided; however, these are exemplary only and should not be regarded as limiting the elements of the present invention.

Example 1

| Sr. No. | Ingredients | Weight (mg)/Capsule |
|---|---|---|
| 1. | *Mucuna pruriens* extract | 40 to 80 mg |
| 2. | *Cynara cardunculus* extract | 90 to 150 mg |
| 3. | *Trigonella foenum graecum* extract | 90 to 150 mg |
| 4. | *Withania somnifera* extract | 90 to 150 mg |
| 5. | L-Arginine | 40 to 80 mg |
| 6. | Microcrystalline Cellulose | 40 to 70 mg |
| 7. | Silicon dioxide | 4 to 8 mg |

Example 2

| Sr. No. | Ingredients | Weight (mg)/Capsule (450 mg) | Weight (gm)/100 gm powder |
|---|---|---|---|
| 1. | *Mucuna pruriens* extract | 50.00 | 11.11 |
| 2. | *Cynara cardunculus* extract | 100.00 | 22.22 |
| 3. | *Trigonella foenum graecum* extract | 100.00 | 22.22 |
| 4. | *Withania somnifera* extract | 100.00 | 22.22 |
| 5. | L-Arginine | 50.00 | 11.11 |
| 6. | Microcrystalline Cellulose | 45.00 | 10.00 |
| 7. | Silicon dioxide | 5.00 | 1.11 |
| | Total | 450.00 | 100.00 |

Example 3

Process for Preparation of Composition of Example 2:
  a) Sieving and weighing 50 mg of *Mucuna pruriens* extract, 100 mg of *Cynara cardunculus* extract, 100 mg of *Trigonella foenum graecum* extract, 100 mg of *Withania somnifera* extract and 50 mg of L-Arginine separately;
  b) blending all the raw material of step (a) for 5 minutes at 25 rpm;
  c) adding 45 mg of microcrystalline cellulose and 5 mg of silicon dioxide into step (b) followed by blending for 10 minutes at 25 rpm to obtained homogenized mixture;
  d) filling the homogenized mixture of step (c) into size 0 transparent capsule using capsule filling machine to obtain final product.

Example 4

| Sr. No. | Ingredients | Weight (mg)/Capsule | Weight (gm)/100 gm |
|---|---|---|---|
| 1. | *Mucuna pruriens* extract | 72.22 | 11.11 |
| 2. | *Cynara cardunculus* extract | 144.44 | 22.22 |
| 3. | *Trigonella foenum graecum* extract | 144.44 | 22.22 |
| 4. | *Withania somnifera* extract | 144.44 | 22.22 |
| 5. | L-Arginine | 72.22 | 11.11 |
| 6. | Micro Crystalline Cellulose | 65.00 | 10.00 |
| 7. | Silicon dioxide | 7.22 | 1.11 |
| | Total | 650.00 | 100.00 |

Example 5

Process for Preparation of Composition of Example 4:
  a) Sieving and weighing 72.22 mg of *Mucuna pruriens* extract, 144.44 mg of *Cynara cardunculus* extract, 144.44 mg of *Trigonella foenum graecum* extract, 144.44 mg of *Withania somnifera* extract and 72.22 mg of L-Arginine separately;
  b) blending all the raw material of step (a) for 5 minutes at 25 rpm;
  c) adding 65 mg of microcrystalline cellulose and 7.22 mg of silicon dioxide into step (b) followed by blending for 10 minutes at 25 rpm to obtained homogenized mixture;
  d) filling the homogenized mixture of step (c) into size 0 transparent capsule using capsule filling machine to obtain final product.

Example 6: Analytical Test Results

Example 2, Coded as OLNP-05 was tested for Total Saponins and total flavonoids by Gravimetric method and UV spec method respectively. The sample (Example 2) was also tested for heavy metals and microbiological parameters viz; total plate count, yeast and mold count, *E. coli* and *Salmonella* content. The results are given in below Table 1.

TABLE 1

| Analytical Test Result of OLNP-05 | | | |
|---|---|---|---|
| Sr. No. | Test Parameters | Test Result | Test Method |
| 1. | Total Saponins | 32.59% | Gravimetric |
| 2. | Total Flavonoids | 2.39% | UV Spec (UV-Vis) |
| 3. | Lead | 0.070 ppm | AOAC 2015.01 by ICP-MS |
| 4. | Arsenic | <0.05 ppm | AOAC 2015.01 by ICP-MS |
| 5. | Mercury | <0.01 ppm | AOAC 2015.01 by ICP-MS |
| 6. | Total Plate Count | 95 cfu/g | ISO 4833-1: 2013 |
| 7. | Total Yeast and Mold Count | <10 cfu/g | ISO 21527-2: 2008 |
| 8. | *E. coli* | Absent/1 g | IS 5887(Part 1): 1976 |
| 9. | *Salmonella* | Absent/25 g | ISO 6579-1: 2017 |

Example 7: Experimental Details

A randomized, double-blind, placebo-control experimentation was designed to assess the efficacy and safety of the present composition (Example 2, coded as OLNP-05) versus placebo for the treatment of subjects with premature ejaculation (PE).

Methods

The experiment was prospectively registered at the Clinical Trials Registry India (Registration No: CTRI/2017/08/009226, Feb. 8, 2017) and received approval from the Institutional Ethics Committee, Maharaja Agrasen Hospital, New Delhi, India prior to commencement of the study.

Total 60 males with PE were enrolled and randomly assigned to receive either OLNP-05 or placebo group. The subjects included in the experiment were provided with study medication for a period of 8 weeks, which includes study visits on day 1, day 28 and day 56. Subjects were advised to take one capsule of Example 2 (450 mg) twice daily. Mean change from baseline in Intra-vaginal Ejaculatory Latency Time (IELT), improvement in Premature Ejaculation Profile (PEP) and Clinical Global Impression-Improvement scale (CGI-I) were used to assess the efficacy of treatment. P value <0.05 was considered significant.

Results

At the end of the treatment, the improvement in IELT score in the OLNP-05 group was significantly higher than the placebo (p<0.05). IELT score was increased from 1.25 min to 6.34 min at final visit in the OLNP-05 group and in placebo group the improvement was from 1.34 min to 1.81 min at the final visit (FIG. 1). The PEP control score was found to be significantly improved from 2.00±0.37 to 4.13±0.57 at final visit in the OLNP-05 group, whereas in the placebo treatment group the improvement was from 2.03±0.18 to 2.30±0.46. Subjects in the OLNP-05 treatment group reported significantly (p<0.05) greater improvement in PEP subscale score includes PEP control, PEP satisfaction, PEP distress and PEP relationship problems (FIG. 2). The mean change from baseline in efficacy criteria is given in below Table 2.

TABLE 2

Mean change from baseline in efficacy criteria

| Visit | OLNP-05 Capsule N = 30 | | Placebo Capsule N = 30 | | P value |
|---|---|---|---|---|---|
| | Mean (SD) | Change from baseline | Mean (SD) | Change from baseline | |
| Mean change in IELT (Min) | | | | | |
| Baseline | 1.25 (0.15) | | 1.34 (0.25) | | |
| Visit 2 | 4.11 (0.60) | 2.86 (0.59)*^ | 1.59 (0.97) | 0.25 (0.93) | <0.0001 |
| Visit 3 | 6.34 (0.87) | 5.09 (0.83)*^ | 1.81 (1.43) | 0.47 (1.35) | <0.0001 |
| Mean change in PEP Control | | | | | |
| Baseline | 2.00 (0.37) | | 2.03 (0.18) | | |
| Visit 2 | 3.03 (0.18) | 1.03 (0.41)*^ | 2.03 (0.18) | 0.00 (0.26) | <0.0001 |
| Visit 3 | 4.13 (0.57) | 2.13 (0.63)*^ | 2.30 (0.46) | 0.27 (0.44) * | <0.0001 |
| Mean change from baseline in PEP Satisfaction Score | | | | | |
| Baseline | 2.40 (0.50) | | 2.20 (0.41) | | |
| Visit 2 | 3.77 (0.43) | 1.37 (0.67)*^ | 2.37 (0.49) | 0.16 (0.50) | <0.0001 |
| Visit 3 | 4.13 (0.57) | 1.73 (0.78)*^ | 2.47 (0.57) | 0.27 (0.58)* | <0.0001 |
| Mean change in PEP Distress Score | | | | | |
| Baseline | 3.63 (0.49) | | 3.73 (0.45) | | |
| Visit 2 | 4.00 (0.26) | 0.37 (0.49)*^ | 3.73 (0.52) | 0.00 (0.59) | 0.0151 |
| Visit 3 | 4.57 (0.57) | 0.93 (0.64)*^ | 3.83 (0.64) | 0.10 (0.71) | <0.0001 |
| Mean change in PEP Relationship problem Score | | | | | |
| Baseline | 3.60 (0.50) | | 3.83 (0.38) | | |
| Visit 2 | 4.07 (0.25) | 0.47 (0.57)* | 3.90 (0.40) | 0.07 (0.25) | 0.0600 |
| Visit 3 | 4.17 (0.38) | 0.57 (0.63)* | 4.00 (0.45) | 0.17 (0.38)* | 0.1286 |
| Mean change from baseline in PEP Index Score | | | | | |
| Baseline | 11.63 (0.72) | | 11.80 (0.61) | | |
| Visit 2 | 14.87 (0.62) | 3.23 (0.97)*^ | 12.03 (0.76) | 0.23 (0.73) | 0.0001 |
| Visit 3 | 17.00 (1.46) | 5.37 (1.61)*^ | 12.60 (1.35) | 0.80 (1.30)* | 0.0001 |

*Statistically significant (p < 0.05) within group;
^statistically significant (2 < 0.05) between group.
Within group analysis by Pair t-test and between group analysis by unpaired t-test.

Improvement in CGI-I in different visits is given in Table 3. A greater proportion of mean in the OLNP-05 treated group, i.e. 19 (63.33%) were found to be 'Much improved' category in the CGI-I assessment.

TABLE 3

Improvement in Clinical Global Impression-Improvement scale in different visits
Improvement in CGI-I in different visits

| | OLNP-05 (N, %) | | Placebo (N, %) | |
|---|---|---|---|---|
| | Visit 2 | Visit 3 | Visit 2 | Visit 3 |
| Not assessed = 0 | — | — | — | — |
| Very much improved = 1 | — | 6 (20.00) | — | — |
| Much improved = 2 | 2 (6.67) | 19 (63.33) | — | — |
| Minimally improved = 3 | 28 (93.33) | 5 (16.67) | 5 (15.67) | 11 (36.67) |
| No change = 4 | — | — | 25 (83.33) | 17 (56.67) |
| Minimally worse = 5 | — | — | — | 2 (6.67) |
| Much Worse = 6 | — | — | — | — |
| Very much worse = 7 | — | — | — | — |

There were no adverse events showing the product OLNP-05 is safe and well tolerated.

Conclusions

The present experiments, demonstrate that the OLNP-05 is more effective compared with placebo in prolonging of IELT, improving in individual parameters of PE score and improvement in Clinical Global Impression. OLNP-05 was found to be safe and well tolerated during the study period.

Example 8: Acute Oral Toxicity Study

The test item OLNP-05 from Example 2 was evaluated for Acute Oral Toxicity in Sprague Dawley rats as per OECD Guidelines for Testing of Chemicals (NO. 425, Section 4: Health Effects) on conduct of "Acute Oral Toxicity-Up-and-Down-Procedure (UDP)" adopted on 3 Oct. 2008. OLNP-05 was found to have LD50 greater than 5000 mg/kg body weight as per OECD Guideline No. 425-Acute Oral Toxicity, which indicates the higher safety profile of the composition.

Methods

The limit test of 5000 mg/kg body weight was performed with three animals (Rats). All the animals were observed for clinical signs of toxicity at 30 to 40 min, 1 hr (±10 mins), 2 hrs (±10 mins), 3 hrs (±10 mins) and 4 hrs (±10 mins) post dosing on day 1 and thereafter once daily for clinical signs of toxicity and twice for mortality during the 14 days observation period.

Results

No clinical signs of toxicity and mortalities were observed at dose of 5000 mg/kg body weight in any of the dosed animals (Tables 4A and 4B). No changes were observed in body weight and percent change in any body weight with respect to Day 1 in all the animals. All the animals in the test revealed physiologically normal increase in body weights during the observation period (Table 5). No gross pathologically changes were observed in any of the animals (Table 6).

TABLE 4A

Individual animal clinical signs of toxicity and mortality on Day 1

| Test | Dose (mg/kg body weight) | Animal No. | Sex | 30-40 min | 1 hr (±10 min) | 2 hrs (±10 min) | 3 hrs (±10 min) | 4 hrs (±10 min) |
|---|---|---|---|---|---|---|---|---|
| Limit Test | 5000 | Rd5681 | F | N | N | N | N | N |
|  |  | Rd5682 | F | N | N | N | N | N |
|  |  | Rd5683 | F | N | N | N | N | N |

F: Female;
N: Normal

TABLE 4B

Individual animal clinical signs of toxicity and mortality record on Days 2 to 15

| Test | Dose (mg/kg body weight) | Animal No. | Sex | Clinical Signs of Toxicity Day | | | | | | | | | | | | | |
|---|---|---|---|---|---|---|---|---|---|---|---|---|---|---|---|---|---|
|  |  |  |  | 2 | 3 | 4 | 5 | 6 | 7 | 8 | 9 | 10 | 11 | 12 | 13 | 14 | 15 |
| Limit Test | 5000 | Rd5681 | F | N | N | N | N | N | N | N | N | N | N | N | N | N | N |
|  |  | Rd5682 | F | N | N | N | N | N | N | N | N | N | N | N | N | N | N |
|  |  | Rd5683 | F | N | N | N | N | N | N | N | N | N | N | N | N | N | N |

F: Female;
N: Normal

TABLE 5

Individual animal body weight (g) and percent change in body weight with respect to Day 1

| Test | Dose (mg/kg body weight) | Animal No. | Sex | Body Weight (g) on Day | | | Percent Change in Body Weight with Respect to Day | |
|---|---|---|---|---|---|---|---|---|
|  |  |  |  | 1 | 8 | 15 | 1 to 8 | 1 to 15 |
| Limit Test | 5000 | Rd5681 | F | 167.50 | 190.14 | 212.64 | 13.52 | 26.95 |
|  |  | Rd5682 | F | 189.62 | 214.49 | 238.27 | 13.12 | 25.66 |
|  |  | Rd5683 | F | 184.96 | 206.11 | 228.90 | 11.43 | 23.76 |

F: Female

TABLE 6

Individual animal gross pathology findings

| Test | Dose (mg/kg body weight) | Animal No. | Sex | Fate | Gross Pathology Findings External | Internal |
|---|---|---|---|---|---|---|
| Limit Test | 5000 | Rd5681 | F | TS | NAD | NAD |
| | | Rd5682 | F | TS | NAD | NAD |
| | | Rd5683 | F | TS | NAD | NAD |

F: Female;
NAD: No Abnormality Detected;
TS: Terminal sacrifice

Conclusion: Under the experiment conditions employed and based on the observed results of experiment, it is concluded that the estimated LD50 of test item OLNP-05 is greater than 5000 mg/kg body weight as per OECD Guideline [No. 425-Acute Oral Toxicity-Up-and-Down Procedure (AOT425 statpgm)], when administered as a single dose by oral gavage to Sprague Dawley Rats. Hence, the test item, OLNP-05 does not fall under classification criteria according to the Globally Harmonized System of Classification and Labelling of Chemicals (GHS).

Example 9: Total Testosterone Study

An experiment was conducted enrolling 3 male cyclists who were dosed with 450 mg of OLNP-05 capsules twice daily for a period of 4 weeks. At the end of the study period total serum testosterone level was evaluated. The results are shown in below Table 7. In Table 7, the free testosterone test measures the amount of unattached, or "free," testosterone in blood. The total testosterone test measures testosterone that is bound to proteins in the blood (e.g., albumin and sex-hormone binding globulin [SHBG]) as well as testosterone that is not bound (free testosterone). Typically, a test for total testosterone is used for diagnosis.

TABLE 7

| Sample | Study duration | Dose | Free testosterone Pre-treatment level | Free testosterone Post treatment levels | % Increase | Total testosterone Pre-treatment level | Total testosterone Post treatment levels | % Increase |
|---|---|---|---|---|---|---|---|---|
| Fenugreek extract | 12 weeks | 600mg/day[1] | 8.17 pg/ml | 11.97 pg/ml | 46.51% | 405.19 ng/dl | 436.34 ng/dl | 7% |
| | 8 weeks | 300 mg of twice daily[2] | 17.76 ng/dl | 35.29 ng/dl | 98.70% | — | — | |
| Mucuna extract | 3 months | 5000 mg/day (Subject normozoospermic)[3] | — | — | — | 4.49 ng/ml | 5.72 ng/ml | 27.39% |
| Cynara extract | — | — | — | — | — | — | — | — |
| Aswa-gandha | 8 weeks | 300 mg of twice daily[4] | — | — | — | 630.45 ng/dl | 726.64 ng/dl | 15.25% |
| | 16 weeks | delivering 21 mg of withanolide glycosides a day[5] | — | — | — | 346.56 pmol/L | 378.38 pmol/L | 9.18% |
| OLNP-05 | 4 weeks | 450 mg of twice daily | 3.285 pg/ml | 9.385 pg/ml | 185.69% | 168.5 ng/dl | 413.0 ng/dl | 145.10% |

1. Maheshwari et al, Int. J. Med. Sci. 2017, Vol 14 58-66.

2. Wankhede et al, Journal of Sport and Health Science 5 (2016) 176-182.

3. Shukla et al., Fertility and Sterility (2009), Vol 92, No. 6, 1934-1940.

4. Wankhede et al., Journal of the International Society of Sports Nutrition (2015) 12; 1-11.

5. Lopresti et al., American Journal of Men's Health (2019) 1-15.

pg/ml-picogram/millilitre ng/dl-nanogram/decilitre

Conclusion: A significant increase in total testosterone level (145.10%) and in free testosterone level (185.69%) was observed from OLNP-05 in the above Table 7.

Example 10: Ejaculation Profile Study

A triple blind, randomized, double dummy, prospective placebo controlled, dose determination study was conducted by the developer (U.S. Pat. No. 9,486,482B2). The capsule composition containing *Withania somnifera* extract 120 mg/capsule and *Mucuna pruriens* extract 50 mg/capsule along with other herbal extracts was studied in 147 subjects [Example 3, Table 6 of U.S. Pat. No. 9,486,482] with male sexual dysfunction (Erectile Dysfunction and/or low libido and sexual dissatisfaction and/or premature ejaculation). Index for Premature Ejaculation, IPE, International Index of Erectile Function IIEF-A, IIEF-B, IIEF (A+B) was evaluated and the data for the IPE is given in the Table 8 below.

TABLE 8

| Sample | Study duration | Dose | Free testosterone | | | Total testosterone | | | Intra-vaginal Vaginal Latency Time (IELT) | Pre-mature ejaculation profile (PEP) | Index for pre-mature ejaculation (IPE) | % improvement in ejaculation profile |
|---|---|---|---|---|---|---|---|---|---|---|---|---|
| | | | Pre-treatment level | Post treatment levels | % Increase | Pre-treatment level | Post treatment levels | % Increase | | | | |
| OLNP-05 | 4 weeks | 450 mg capsules twice daily | 3.285 pg/ml | 9.385 pg/ml | 185.69% | 168.5 ng/dl | 413.0 ng/dl | 145.10% | 1.25 min to 6.34 min | 2.00 ± 0.37 to 4.13 ± 0.57 | — | 106.50% |
| Example 3, Table 6 of US94564S2 | 2 month | 520 mg capsules twice daily | — | — | — | 513.44 | 430.57 | −0.00% | — | — | 26.88 ± 5.93 to 39.23 ± 5.77 | 42.30% |

Conclusion: The study indicates that the percentage improvement in the ejaculation profile is better in OLNP-05 (106.50%) compare to the capsule composition of U.S. Pat. No. 9,486,482 (42.30%).

REFERENCE

1. Kavitha and Thangamani. 2014. Amazing bean "*Mucuna pruriens*": A comprehensive review. Journal of Medicinal Plants Research. Vol. 8. p. 138-143.
2. Chauhan Sharma, Dixit and Thakur. 2014. A Review on Plants Used for Improvement of Sexual Performance and Virility. BioMed Research International. Vol. 2014.
3. Bichitra N Nayak and Harpal S Buttar. Herbal therapy for men with erectile dysfunction. Curr Res Cardiol 2015; 2(1):30-34.
4. S. E. Althof, C. G. McMahon, M. D. Waldinger, et al. An update of the International Society of Sexual Medicine's guidelines for the diagnosis and treatment of premature ejaculation (PE) The Journal of Sexual Medicine, 11 (2014), pp. 1392-1422.
5. E. C. Serefoglu, C. G. McMahon, M. D. Waldinger, et al. An evidence-based unified definition of lifelong and acquired premature ejaculation: Report of the Second International Society for Sexual Medicine Ad Hoc Committee for the definition of premature ejaculation The Journal of Sexual Medicine, 11 (2014), pp. 1423-1441.

We claim:

1. A dosage form comprising an herbal composition consisting of an extract of *Mucuna pruriens*, an extract of *Cynara cardunculus*, an extract of *Trigonella foenum graecum*, an extract of *Withania somnifera*, L-arginine, and a pharmaceutically acceptable excipient, wherein the herbal composition meets at least one of the following conditions:
the extract of *Mucuna pruriens* and at least one of the extract of *Cynara cardunculus*, the extract of *Trigonella foenum graecum*, and the extract of *Withania somnifera* are present in the herbal composition in a first ratio of 1:2 by weight; and
the extract of *Cynara cardunculus* and at least one of the extract of *Trigonella foenum graecum*, and the extract of *Withania somnifera* are present in the herbal composition in a second ratio of 1:1 by weight;

wherein the dosage form is selected from the group consisting of tablets, capsules, and pills.

2. The dosage form as claimed in claim 1, wherein the extract of *Mucuna pruriens* and the extract of *Cynara cardunculus* are present in the herbal composition in the first ratio of 1:2 by weight.

3. The dosage form as claimed in claim 2, wherein the extract of *Mucuna pruriens* and at least one of the extract of *Trigonella foenum graecum* and the extract of *Withania somnifera* are present in the herbal composition in the first ratio of 1:2 by weight.

4. The dosage form as claimed in claim 1, wherein the extract of *Mucuna pruriens* and the extract of *Trigonella foenum graecum* are present in the herbal composition in the first ratio of 1:2 by weight.

5. The dosage form as claimed in claim 1, wherein the extract of *Mucuna pruriens* and the extract of *Withania somnifera* are present in the herbal composition in the first ratio of 1:2 by weight.

6. The dosage form as claimed in claim 1, wherein the extract of *Cynara cardunculus* and the extract of *Trigonella foenum graecum* are present in the herbal composition in the second ratio of 1:1 by weight.

7. The dosage form as claimed in claim 1, wherein the extract of *Cynara cardunculus* and the extract of *Withania somnifera* are present in the herbal composition in the second ratio of 1:1 by weight.

8. The dosage form as claimed in claim 1, wherein the extract of *Trigonella foenum graecum* and the extract of *Withania somnifera* are present in the herbal composition in the second ratio of 1:1 by weight.

9. A dosage form comprising an herbal composition, wherein said herbal composition comprises:
   a) an extract of *Mucuna pruriens* in an amount of 40 to 80 mg;
   b) an extract of *Cynara cardunculus* in an amount of 90 to 150 mg;
   c) an extract of *Trigonella foenum graecum* in an amount of 90 to 150 mg;
   d) an extract of *Withania somnifera* in an amount of 90 to 150 mg;
   e) L-arginine in an amount of 40 to 80 mg; and
   f) a pharmaceutically acceptable excipient; and
   wherein the herbal composition is present in an amount effective to treat a low Intra-vaginal Ejaculatory Latency Time (IELT) score or a low Premature Ejaculation Profile (PEP) score;
   wherein said dosage form is selected from the group consisting of tablets, capsules, and pills.

10. The dosage form as claimed in claim 9, wherein said herbal composition comprises:
   a) the extract of *Mucuna pruriens* in an amount of 50 to 72 mg;
   b) the extract of *Cynara cardunculus* in an amount of 100 to 144 mg;
   c) the extract of *Trigonella foenum graecum* in an amount of 100 to 144 mg;
   d) the extract of *Withania somnifera* in an amount of 100 to 144 mg; and
   e) L-arginine in an amount of 50 to 72 mg.

11. The dosage form as claimed in claim 9, wherein said herbal composition comprises:
   a) the extract of *Mucuna pruriens* in an amount of 50 mg;
   b) the extract of *Cynara cardunculus* in an amount of 100 mg;
   c) the extract of *Trigonella foenum graecum* in an amount of 100 mg;
   d) the extract of *Withania somnifera* in an amount of 100 mg; and
   e) L-arginine in an amount of 50 mg.

12. The dosage form as claimed in claim 9, wherein said pharmaceutically acceptable excipient is selected from the group consisting of binders, glidants, lubricants, diluents, disintegrants, emulsifying agents, anti-caking agents, anti-adherents, granulating agents, flavors and mixtures thereof.

13. The dosage form as claimed in claim 12, wherein said pharmaceutically acceptable excipient comprises a mixture of 40 to 70 mg Microcrystalline Cellulose and 4 to 8 mg Silicon dioxide.

14. The dosage form as claimed in claim 9, wherein said pharmaceutically acceptable excipient is present in the dosage form in an amount of 40 mg to 100 mg.

15. A process for preparation of an herbal composition as claimed in claim 1, comprising;
   a) sieving and weighing the extract of *Mucuna pruriens*, the extract of *Cynara cardunculus*, the extract of *Trigonella foenum graecum*, the extract of *Withania somnifera*, and L-Arginine;
   b) after the step of sieving and weighing, blending the extract of *Mucuna pruriens*, the extract of *Cynara cardunculus*, the extract of *Trigonella foenum graecum*, the extract of *Withania somnifera*, and L-Arginine for 5 minutes at 25 rpm to produce a blended mixture;
   c) adding the pharmaceutically acceptable excipient to the blended mixture, followed by blending for 10 minutes at 25 rpm to obtain a homogenized mixture; and
   d) filling the homogenized mixture into a capsule shell to obtain the dosage form.

16. A process for preparation of an herbal composition as claimed in claim 9, comprising;
   a) sieving and weighing the extract of *Mucuna pruriens*, the extract of *Cynara cardunculus*, the extract of *Trigonella foenum graecum*, the extract of *Withania somnifera*, and L-Arginine;
   b) after the step of sieving and weighing, blending the extract of *Mucuna pruriens*, the extract of *Cynara cardunculus*, the extract of *Trigonella foenum graecum*, the extract of *Withania somnifera*, and L-Arginine for 5 minutes at 25 rpm to produce a blended mixture;
   c) adding the pharmaceutically acceptable excipient to the blended mixture, followed by blending for 10 minutes at 25 rpm to obtain a homogenized mixture; and
   d) filling the homogenized mixture into a capsule shell to obtain the dosage form.

17. A method of treating a sexual disorder by at least one of increasing testosterone levels, enhancing erection, reducing anxiety, and delaying ejaculation, comprising administering an herbal composition as claimed in claim 1 to a subject in need thereof.

18. A method of treating a sexual disorder by at least one of increasing testosterone levels, enhancing erection, reducing anxiety, and delaying ejaculation, comprising administering an herbal composition as claimed in claim 9 to a subject in need thereof.

19. A dosage form comprising an herbal composition comprising an extract of *Mucuna pruriens*, an extract of *Cynara cardunculus*, an extract of *Trigonella foenum graecum*, an extract of *Withania somnifera*, L-arginine, and a pharmaceutically acceptable excipient,
   wherein the herbal composition meets at least one of the following conditions:
      L-arginine and the extract of *Mucuna pruriens* are present in a first ratio of 1:1 by weight; and
      L-arginine and at least one of the extract of *Cynara cardunculus*, the extract of *Trigonella foenum graecum*, and the extract of *Withania somnifera* are present in the herbal composition in a second ratio of 1:2 by weight; and
   wherein the herbal composition is present in an amount effective to treat a low Intra-vaginal Ejaculatory Latency Time (IELT) score or a low Premature Ejaculation Profile (PEP) score;
   wherein said dosage form is selected from the group consisting of tablets, capsules, and pills.

20. A dosage form comprising an herbal composition consisting of:
   a first extract selected from the group consisting of an extract of *Mucuna pruriens*, an extract of *Rhodiola rosea*, an extract of horny goat weed, an extract of *Asparagus racemosus*, an extract of *Hypericum perforatum*, an extract of *Butea superba*, an extract of *Griffonia simplicifolia*, an extract of *muira puma*, an extract of Damiana, and a mixture thereof;
   an extract of *Cynara cardunculus*,
   an extract of *Trigonella foenum graecum*,
   an extract of *Withania somnifera*,
   L-arginine, and
   a pharmaceutically acceptable excipient,
   wherein:
      the extract of *Cynara cardunculus* and at least one of the extract of *Trigonella foenum graecum* and the extract of *Withania somnifera* are present in the herbal composition in a second ratio of 1:1 by weight;

the extract of *Trigonella foenum graecum* and the extract of *Withania somnifera* are present in the herbal composition in the second ratio of 1:1 by weight; and/or the first extract and at least one of the extract of *Cynara cardunculus*, the extract of *Trigonella foenum graecum*, and the extract of *Withania somnifera* are present in the herbal composition in a first ratio of 1:2 by weight;

wherein the dosage form is selected from the group consisting of tablets, capsules, and pills.

* * * * *